(12) United States Patent
Stürm et al.

(10) Patent No.: US 10,398,146 B2
(45) Date of Patent: Sep. 3, 2019

(54) CALCIUM CARBONATE FOR PLANT PROTECTION

(71) Applicant: Omya International AG, Oftringen (CH)

(72) Inventors: Christoph Stürm, Olten (CH); Wulff Hansen, Safenwil (CH)

(73) Assignee: Omya International AG, Oftringen (CH)

(*) Notice: Subject to any disclaimer, the term of this patent is extended or adjusted under 35 U.S.C. 154(b) by 20 days.

(21) Appl. No.: 15/535,160

(22) PCT Filed: Dec. 15, 2015

(86) PCT No.: PCT/EP2015/079871
§ 371 (c)(1),
(2) Date: Jun. 12, 2017

(87) PCT Pub. No.: WO2016/096907
PCT Pub. Date: Jun. 23, 2016

(65) Prior Publication Data
US 2017/0360046 A1 Dec. 21, 2017

Related U.S. Application Data

(60) Provisional application No. 62/095,863, filed on Dec. 23, 2014.

(30) Foreign Application Priority Data

Dec. 16, 2014 (EP) ..................................... 14198305

(51) Int. Cl.
| | |
|---|---|
| *A01N 59/06* | (2006.01) |
| *A01N 25/04* | (2006.01) |
| *A01N 25/14* | (2006.01) |
| *A01N 43/54* | (2006.01) |
| *A01N 43/36* | (2006.01) |
| *A01N 47/16* | (2006.01) |
| *A01N 43/40* | (2006.01) |
| *A01N 37/24* | (2006.01) |
| *A01N 43/22* | (2006.01) |
| *A01N 53/00* | (2006.01) |

(52) U.S. Cl.
CPC ............. *A01N 59/06* (2013.01); *A01N 25/04* (2013.01); *A01N 25/14* (2013.01); *A01N 37/24* (2013.01); *A01N 43/22* (2013.01); *A01N 43/40* (2013.01); *A01N 43/54* (2013.01); *A01N 47/16* (2013.01); *A01N 53/00* (2013.01)

(58) Field of Classification Search
None
See application file for complete search history.

(56) References Cited

U.S. PATENT DOCUMENTS

| | | |
|---|---|---|
| 2005/0014930 A1 | 1/2005 | Koyama et al. |
| 2007/0031507 A1 | 8/2007 | Koyama et al. |
| 2009/0280201 A1 | 11/2009 | Navarro et al. |
| 2012/0031576 A1 | 2/2012 | Gane et al. |

FOREIGN PATENT DOCUMENTS

| | | |
|---|---|---|
| EP | 2371766 A1 | 11/1989 |
| EP | 2070991 A1 | 6/2009 |
| EP | 2264108 A1 | 12/2010 |
| EP | 2264109 A1 | 12/2010 |
| EP | 2447213 A1 | 5/2012 |
| EP | 2524898 A1 | 11/2012 |
| JP | S59224629 A | 12/1984 |
| JP | H0680511 A | 3/1994 |
| JP | H0692812 A | 4/1995 |
| JP | 2001199818 A | 7/2001 |
| WO | 9838867 A1 | 9/1998 |
| WO | 2009074492 A1 | 6/2009 |
| WO | 2013142473 A1 | 9/2013 |

OTHER PUBLICATIONS

International Search Report dated Mar. 3, 2016 for PCT/EP2015/079871.
Written Opinion of the International Searching Authority dated Mar. 3, 2016 for PCT/EP2015/079871.
Ataee et al. "Antibacterial effect of calcium carbonate nanoparticles on Agrobacterium tumefaciens". Iranian Journal of Military Medicine, Jun. 1, 2011 (2011-86-81) pp. 65-70. Retrieved from the Internet: www.militarymedj.ir/files/site1/user_files_01eb20/eng/ataee-A-10-57-5-617485c.pdf.
Burford et al. "Geomycology: fungi in mineral substrata". Mycologist, vol. 17. No. 3. Aug. 1, 2003 (Aug. 1, 2003) pp. 98-107. Abstract Only.
Yee "Behavioural responses by Rhagoletis indifferens (Dipt.,Tephritidae) to sweet cherry treated with kaolin- and limestone-based products". Journal of Applied Entomology. vol. 136. No. 1-2. Feb. 29, 2012 (Feb. 29, 2012), pp. 124-132.
Prager et al. "Oviposition and feeding by Bactericera cockerelli (Homoptera: Psyllidae) in response to a solar protectant applied to potato plants". Crop Protection. vol. 45. Mar. 1, 2013 (Mar. 1, 2013), pp. 57-62. Abstract Only.
Yoon et al. "The Suppressive Effects of Calcium Compounds against Botrytis cinerea in Paprika". Kor. J. Hort. Sci. Technol. vol. 28. No. 28, Dec. 1, 2010 (Dec. 1, 2010), pp. 1072-1077.
D6—Database WPI, Week 198505, Thomson Scientific, AN 1985-028797, XP002737187.
D7—Database WPI, Week 199416, Thomson Scientific, AN 1994-131930, XP002737188.
D8—Database WPI, Week 199418, Thomson Scientific, AN 1994-147823, XP002737189.
D9—Database WPI, Week 200170, Thomson Scientific, AN 2001-609448, XP002737190.
Nigro et al. "Control of table grape storage rots by pre-harvest applications of salts," Postharvest Biology and Technology, 2006, 42, 142-149. Abstract Only.
Abdel-Mageed et al. Journal of Biological Chemistry and Environmental Science, 2012, 7(2), 617-634.

*Primary Examiner* — Alton N Pryor
(74) *Attorney, Agent, or Firm* — Schwegman Lundberg & Woessner, P.A.

(57) ABSTRACT

The present invention relates to the use of calcium carbonate as plant protection product for topical, pre-harvest application, wherein the plant protection product controls a pest during plant growth.

28 Claims, No Drawings

CALCIUM CARBONATE FOR PLANT PROTECTION

CROSS-REFERENCE TO RELATED APPLICATIONS

This is a U.S. national phase of PCT Application No. PCT/EP2015/079871, filed Dec. 15, 2015, which claims priority to European Application No. 14198305.6, filed Dec. 16, 2014 and U.S. Provisional Patent Application No. 62/095,863, filed Dec. 23, 2014.

The present invention relates to the field of plant protection products, and especially to a plant protection product which can be applied before harvesting as well as a method for protecting plants during growth involving the use of calcium carbonate.

Plants and especially agricultural crops are often subjected to a variety of pathogens or pests, which can affect the yield and quality of the products.

Grapes, for example, can be attacked by a number of fungi, fungus-like organisms and insects which affect the berries and cause loss of quality and influence the taste of the later produced wine. Aside from leaves, most grape pathogens also infect inflorescences, clusters and berries so that the yield can be reduced. Insects may infect the berries as well in that they deposit on the surface or inside the berry their eggs, which grow to larvae. Said berry infections typically result in decay of fruit tissue and alteration of the fruit juices, however, specific effects on berry quality depend on the ripening stage at which the infection occurs.

For example, the gray mould caused by the fungus *Botrytis cinerea* is one of the serious diseases of grapes and more than 200 other plant species. Berries damaged by insects or splitting, due to pre-harvest expansion and/or rain, are common injury sites attacked by *Botrytis cinerea*. Furthermore, the proliferation of gray mould is promoted by consistently wet or humid conditions, and typically results in the loss of the affected bunches.

Another serious threat to grapes and other fruits, especially cherries, blueberries, nectarines, pears, plums, pluots, peaches, raspberries, and strawberries is *Drosophila suzukii*, commonly called the spotted-wing *drosophila*, which is closely related to *Drosophila melanogaster* (the common vinegar fly). *Drosophila suzukii* is an Asian pest of fruit crops which has almost simultaneously been introduced into North America and in Italy in 2008 and 2009, respectively, and currently spreads into the other European countries. It is one of the very few *Drosophila* species which are able to feed on healthy ripening fruit while they are still attached to the plant. Damage is caused by larvae feeding on fruit pulp inside the fruit and berries. Very rapidly, infested fruit begin to collapse around the feeding site. Thereafter, secondary fungal infections, e.g. by *Botrytis cinerea*, or bacterial infections may contribute to further fruit deterioration or rotting.

The aforementioned threats and other plant pests are often tried to combat by the use of pesticides. However, many of these compounds are highly toxic and persistent in the environment, and thus, pesticide use raises a number of concerns. For examples, pesticides can cause water pollution and soil contamination, reduce biodiversity or threaten endangered species. Furthermore, pesticides may cause acute and delayed health effects in workers who are exposed and may result in contamination of the treated product, especially if they are not applied correctly.

Due to these downsides of conventional synthetic pesticides and the growing demand for products from organic farming, alternative ways of protecting plants from pests are becoming increasingly popular.

US 2009/0280201 A1 describes the use of a quillay extract to treat and prevent the infestation with *Botrytis cinerea*. The activity of 19 inorganic and organic salts to control table grape storage rots was investigated in the publication of Nigro et al., Postharvest Biology and Technology, 2006, 42, 142-149. Abdel-Mageed et al., Journal of Biological Chemistry and Environmental Science, 2012, 7(2), 617-634, evaluated the efficiency of several inorganic salts and commercial disinfectants on the inhibition of mycelial growth and sclerotial formation of *Botrytis cinerea* and *Sclerotinia sclerotiorum*. The tested substances were applied before harvesting in order to control said pests during storage. The suppressive effects of calcium compounds against *Botrytis cinerea* in paprika was studied in Yoon et al., Korean Journal of Horticultural Science & Technology, 2010, 28(6), 1072-1077. In said study, calcium compounds were administered systemically to plants via nutrient solutions.

However, there is still a need in the art for further nontoxic alternatives for protecting plants, and especially crops, from pests.

Accordingly, it is an object of the present invention, to provide a plant protection product which can control pests, and especially fungi and insects. It would be desirable that said plant protection product is neither toxic nor persistent in the environment. It would also be desirable that said plant protection product can be applied to crops during growth periods, in which the application of conventional synthetic pesticides is typically prohibited to avoid toxic residues in the crops. It would also be desirable that the plant protection product does not affect the quality of the crops, and products obtained by further processing said crops.

The foregoing and other objects are solved by the subject-matter as defined herein in the independent claims.

According to one aspect of the present invention, use of calcium carbonate as plant protection product for topical, pre-harvest application is provided, wherein the plant protection product controls a pest during plant growth.

According to another aspect of the present invention, a method of protecting a plant by controlling a pest during plant growth is provided, wherein the method comprises the step of topically applying calcium carbonate onto at least a part of a plant before harvesting.

Advantages contained in the embodiment of the present invention are defined in the corresponding sub-claims.

According to one embodiment the pest is a fungus, preferably *Botrytis* and/or *Sclerotinia*, more preferably *Botrytis cinerea*, and/or the pest is an insect, preferably *Drosophila suzukii*. According to another embodiment the calcium carbonate is a natural ground calcium carbonate, a precipitated calcium carbonate, a functionalized calcium carbonate, a calcium carbonate containing mineral, or a mixture thereof, preferably the calcium carbonate is a natural ground calcium carbonate, more preferably the calcium carbonate is selected from the group consisting of marble, chalk, dolomite, limestone, and mixtures thereof, and most preferably the calcium carbonate is limestone.

According to one embodiment the calcium carbonate is in form of particles having a weight median particle size $d_{50}$ from 0.1 to 200 µm, preferably from 0.6 to 100 µm, more preferably from 8.0 to 50 µm, and most preferably from 1 to 50 µm. According to another embodiment the calcium carbonate is used in form of a powder and/or an aqueous suspension, preferably in form of an aqueous suspension having a solids content from 1 to 85 wt.-%, more preferably from 5 to 50 wt.-%, and most preferably from 10 to 25 wt.-%, based on the total weight of the aqueous suspension.

According to one embodiment the calcium carbonate is used in form of a composition, preferably comprising further alkaline salts and/or earth alkaline salts, and more preferably comprising sodium carbonate, sodium bicarbonate, potassium carbonate, magnesium carbonate, calcium chloride, calcium sulphate, calcium nitrate, calcium oxide, calcium hydroxide, or mixtures thereof. According to another embodiment the calcium carbonate is used in combination with an additional plant protection product, preferably a fungicide and/or an insecticide.

According to one embodiment the plant protection product is for plants selected from the group consisting of rosaceae, theobroma cacao, grapes, stone fruits, pome fruits, berries, citrus fruits, legumes, solanaceae crops, brassicaceae crops, cucurbit crops, liliaceous crops, bananas, papayas, mangos, and passion fruits, preferably selected from the group consisting of grapes, stone fruits, pome fruits, berries, citrus fruits, bananas, papayas, mangos, and passion fruits, and most preferably grapes. According to another embodiment the plant protection product controls a pest during plant growth and plant storage.

According to one embodiment the calcium carbonate is in form of an aqueous suspension, and is applied onto at least a part of the plant by spraying. According to another embodiment the calcium carbonate is in form of a powder and is applied onto at least a part of the plant by dusting. According to still another embodiment the calcium carbonate is applied in an amount from 500 mg/m$^2$ to 50 g/m$^2$ of planted field area, preferably from 1 g/m$^2$ to 25 g/m$^2$ of planted field area, and more preferably from 8 g/m$^2$ to 16 g/m$^2$ of planted field area.

According to one embodiment the calcium carbonate is applied at least one time, preferably at least two times, before harvesting. According to another embodiment the calcium carbonate is additionally applied after harvesting, preferably at least one time, more preferably at least two times.

It should be understood that for the purpose of the present invention, the following terms have the following meaning:

The expression "control(s) a pest" or "controlling a pest" as used herein comprises preventing, treating or reducing a pest, inhibiting the rate and extent of a pest attack, or delaying the onset of a pest attack.

For the purpose of the present invention the term "pest" refers to any species, strain or biotype of plant, animal or pathogen injurious to plants or plant products. Examples for a pest are insects, nematodes, parasites, gastropods, weeds, or pathogens such as fungi, viruses, or bacteria.

"Natural ground calcium carbonate" (GCC) in the meaning of the present invention is a calcium carbonate obtained from natural sources, such as limestone, marble, or chalk, and processed through a wet and/or dry treatment such as grinding, screening and/or fractionation, for example by a cyclone or classifier.

"Precipitated calcium carbonate" (PCC) in the meaning of the present invention is a synthesized material, generally obtained by precipitation following a reaction of carbon dioxide and calcium hydroxide (hydrated lime) in an aqueous environment or by precipitation of a calcium- and a carbonate source in water. Additionally, precipitated calcium carbonate can also be the product of introducing calcium and carbonate salts, calcium chloride and sodium carbonate for example, in an aqueous environment. PCC may be vaterite, calcite or aragonite. PCCs are described, for example, in EP 2 447 213 A1, EP 2 524 898 A1, EP 2 371 766 A1, or WO 2013/142473 A1.

"Functionalized calcium carbonate" (FCC) in the meaning of the present invention may feature a natural ground or precipitated calcium carbonate with an internal structure modification or a surface-reaction product, i.e. "surface-reacted calcium carbonate". A "surface-reacted calcium carbonate" is a material comprising calcium carbonate and insoluble, preferably at least partially crystalline, calcium salts of anions of acids on the surface. Preferably, the insoluble calcium salt extends from the surface of at least a part of the calcium carbonate. The calcium ions forming said at least partially crystalline calcium salt of said anion originate largely from the starting calcium carbonate material. FCCs are described, for example, in US 2012/0031576 A1, WO 2009/074492 A1, EP 2 264 109 A1, EP 2 070 991 A1, or EP 2 264 108 A1.

Throughout the present document, the "particle size" of calcium carbonate, or other particulate material is described by its distribution of particle sizes. The value $d_x$ represents the diameter relative to which x % by weight of the particles have diameters less than $d_x$. This means that the $d_{20}$ value is the particle size at which 20 wt.-% of all particles are smaller, and the $d_{98}$ value is the particle size at which 98 wt.-% of all particles are smaller. The $d_{98}$ value is also designated as "top cut". The $d_{50}$ value is thus the weight median particle size, i.e. 50 wt.-% of all grains are bigger whilst the remaining 50 wt.-% are smaller than this particle size. For the purpose of the present invention the particle size is specified as weight median particle size $d_{50}$ unless indicated otherwise. For determining the weight median particle size $d_{50}$ value or the top cut particle size $d_{98}$ value a Sedigraph 5100 or 5120 device from the company Micromeritics, USA, can be used. The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

For the purpose of the present invention, the "solids content" of a liquid composition is a measure of the amount of material remaining after all the solvent or water has been evaporated.

For the purpose of the present invention, the term "viscosity" or "Brookfield viscosity" refers to Brookfield viscosity. The Brookfield viscosity is for this purpose measured by a Brookfield (Type RVT) viscometer at 25° C.±1° C. at 100 rpm using an appropriate spindle of the Brookfield RV-spindle set and is specified in mPa·s. Based on his technical knowledge, the skilled person will select a spindle from the Brookfield RV-spindle set which is suitable for the viscosity range to be measured. For example, for a viscosity range between 200 and 800 mPa·s the spindle number 3 may be used, for a viscosity range between 400 and 1600 mPa·s the spindle number 4 may be used, and for a viscosity range between 800 and 3200 mPa·s the spindle number 5 may be used.

A "suspension" or "slurry" in the meaning of the present invention comprises insoluble solids and a solvent or liquid, preferably water, and optionally further additives, and usually contains large amounts of solids and, thus, is more viscous and can be of higher density than the liquid from which it is formed.

Where the term "comprising" is used in the present description and claims, it does not exclude other non-specified elements of major or minor functional importance.

For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

According to the present invention, use of calcium carbonate as plant protection product for topical, pre-harvest application is provided. The plant protection product controls a pest during plant growth.

In the following details and preferred embodiments of the inventive use will be set out in more details. It is to be understood that these technical details and embodiments also apply to the inventive method.

Calcium Carbonate

The calcium carbonate used according to the present invention may be selected from a natural ground calcium carbonate, a precipitated calcium carbonate, a functionalized calcium carbonate, a calcium carbonate containing mineral, or a mixture thereof.

Natural ground calcium carbonate (GCC) is understood to be manufactured from a naturally occurring form of calcium carbonate, mined from sedimentary rocks such as limestone or chalk, or from metamorphic marble rocks, eggshells or seashells. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Ground calcium carbonate is almost exclusively of the calcitic polymorph, which is said to be trigonal-rhombohedral and represents the most stable of the calcium carbonate polymorphs. The term "source" of the calcium carbonate in the meaning of the present application refers to the naturally occurring mineral material from which the calcium carbonate is obtained. The source of the calcium carbonate may comprise further naturally occurring components such as magnesium carbonate, alumino silicate etc.

According to one embodiment of the present invention the source of natural ground calcium carbonate (GCC) is selected from marble, chalk, dolomite, limestone, or mixtures thereof. Preferably, the source of natural ground calcium carbonate is selected from limestone. According to one embodiment of the present invention the GCC is obtained by dry grinding. According to another embodiment of the present invention the GCC is obtained by wet grinding and subsequent drying.

"Dolomite" in the meaning of the present invention is a calcium carbonate containing mineral, namely a carbonic calcium-magnesium-mineral, having the chemical composition of $CaMg(CO_3)_2$ ("$CaCO_3 \cdot MgCO_3$"). A dolomite mineral may contain at least 30.0 wt.-% $MgCO_3$, based on the total weight of dolomite, preferably more than 35.0 wt.-%, and more preferably more than 40.0 wt.-% $MgCO_3$.

According to one embodiment of the present invention, the calcium carbonate comprises one type of natural ground calcium carbonate. According to another embodiment of the present invention, the calcium carbonate comprises a mixture of two or more types of natural ground calcium carbonates selected from different sources.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation by combining calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the calcium carbonate comprises one type of precipitated calcium carbonate. According to another embodiment of the present invention, the calcium carbonate comprises a mixture of two or more precipitated calcium carbonates selected from different crystalline forms and different polymorphs of precipitated calcium carbonate. For example, the at least one precipitated calcium carbonate may comprise one PCC selected from S-PCC and one PCC selected from R-PCC.

A functionalized calcium carbonate (FCC) may feature a GCC or PCC with a surface and/or internal structure modification. A surface-reacted calcium carbonate may be prepared, for example, by providing a GCC or PCC in form of an aqueous suspension, and adding an acid to said suspension. Suitable acids are, for example, sulphuric acid, hydrochloric acid, phosphoric acid, citric acid, oxalic acid, or a mixture thereof. In a next step, the calcium carbonate is treated with gaseous carbon dioxide. If a strong acid such as sulphuric acid or hydrochloric acid is used for the acid treatment step, the carbon dioxide will form automatically in situ. Alternatively or additionally, the carbon dioxide can be supplied from an external source. Surface-reacted calcium carbonates are described, for example, in US 2012/0031576 A1, WO 2009/074492 A1, EP 2 264 109 A1, EP 2 070 991 A1, or EP 2 264 108 A1. The surface-reacted calcium carbonate, if present, is used unloaded. In other words, the surface-reacted calcium carbonate is not used as a carrying agent. According to one embodiment, the functionalized calcium carbonate is a surface-reacted calcium carbonate, preferably obtained from the reaction with sulphuric acid, hydrochloric acid, phosphoric acid, citric acid, oxalic acid, or a mixture thereof, and carbon dioxide.

According to one embodiment of the present invention, the calcium carbonate is a natural ground calcium carbonate.

According to another embodiment of the present invention, the calcium carbonate is a precipitated calcium carbonate. According to still another embodiment of the present invention, the calcium carbonate is a mixture of natural ground calcium carbonate and precipitated calcium carbonate.

According to one preferred embodiment of the present invention, the calcium carbonate is natural ground calcium carbonate, preferably the calcium carbonate is selected from the group consisting of marble, chalk, dolomite, limestone, and mixtures thereof, and most preferably the calcium carbonate is limestone.

According to one embodiment, the calcium carbonate is in form of particles having a weight median particle size $d_{50}$ from 0.1 to 200 μm, preferably from 0.6 to 100 μm, more preferably from 8.0 to 50 μm, and most preferably from 1 to 50 μm.

The calcium carbonate may be used in any suitable liquid or dry form. For example, the calcium carbonate may be in form of a powder and/or a suspension. The suspension can be obtained by mixing particles of calcium carbonate with a solvent, preferably water. The calcium carbonate to be mixed with a solvent, and preferably water, may be provided in any form, for example, as suspension, slurry, dispersion, paste, powder, a moist filter cake or in pressed or granulated form.

The suspension can be undispersed or dispersed, i.e. the suspension includes a dispersant, and thus, forms an aqueous dispersion.

According to one embodiment of the present invention, the calcium carbonate is used in form of an aqueous suspension, which does not contain a dispersant. According to another embodiment of the present invention, calcium carbonate is used in form of an aqueous suspension, which contains a dispersant. A suitable dispersant may be selected from the group comprising homopolymers or copolymers of polycarboxylic acid salts based on, for example, acrylic acid, methacrylic acid, maleic acid, fumaric acid or itaconic acid and acrylamide or mixtures thereof. Homopolymers or copolymers of acrylic acid are especially preferred. The weight average molecular weight $M_w$ of such products is preferably in the range from 2 000 to 15 000 g/mol, with a weight average molecular weight $M_w$ from 3 000 to 7 000 g/mol or from 3 500 to 6 000 g/mol being especially preferred. According to an exemplary embodiment, the dispersant is sodium polyacrylate having a weight average molecular weight $M_w$ from 2 000 to 15 000 g/mol, preferably from 3000 to 7 000 g/mol, and most preferably from 3 500 to 6 000 g/mol.

The solids content of the suspension of calcium carbonate can be adjusted by the methods known to the skilled person. To adjust the solids content of an aqueous suspension, for example, the aqueous suspension may be partially dewatered by a settling, filtration, centrifugation or thermal separation process. According to one embodiment of the present invention, the solids content of the suspension is from 1 to 85 wt.-%, more preferably from 5 to 50 wt.-%, and most preferably from 10 to 25 wt.-%, based on the total weight of the suspension.

According to one embodiment, the calcium carbonate is in form of an aqueous suspension. The term "aqueous" suspension refers to a system, wherein the liquid phase or solvent of the suspension comprises, preferably consists of, water. However, said term does not exclude that the aqueous suspension comprises an organic solvent selected from the group comprising alcohols such as methanol, ethanol, isopropanol, carbonyl-group containing solvents such as ketones, e.g. acetone or aldehydes, esters such as isopropyl acetate, carboxylic acids such as formic acid, sulphoxides such as dimethyl sulphoxide, and mixtures thereof. If the aqueous suspension comprises an organic solvent, the aqueous suspension comprises the organic solvent in an amount up to 40.0 wt.-% preferably from 1.0 to 30.0 wt.-% and most preferably from 1.0 to 25.0 wt.-%, based on the total weight of the liquid phase of the aqueous suspension. For example, the liquid phase of the aqueous suspension consists of water. If the liquid phase of the aqueous suspension consists of water, the water to be used can be any water available such as tap water and/or deionised water.

According to one embodiment of the present invention, the calcium carbonate is used in form of an aqueous suspension having a solids content from 1 to 85 wt.-%, more preferably from 5 to 50 wt.-%, and most preferably from 10 to 25 wt.-%, based on the total weight of the aqueous suspension. According to a preferred embodiment, the calcium carbonate is used in form of a powder or an aqueous suspension and has a weight median particle size $d_{50}$ from 0.1 to 200 μm, preferably from 0.6 to 100 μm, more preferably from 8.0 to 50 μm, and most preferably from 1 to 50 μm.

Use as Plant Protection Product

According to the present invention use of calcium carbonate as plant protection product for topical, pre-harvest application is provided, wherein the plant protection product controls a pest during plant growth.

A "plant protection product" in the meaning of the present invention is a substance which in general protects plants from any species, strain or biotype of plant, animal, or pathogen injurious to plants or plant products. The term "plant" as used herein encompasses not only a whole plant but also parts of the plant such as roots, stems, leaves, needles, flowers, nuts or fruits. The plant can be a wild plant or a cultivated plant or crop.

It is a requirement of the present invention that the calcium carbonate is applied to the plant topically and before harvesting. "Topical" application refers to a non-systemic application of the plant protection product, i.e. an external or superficial application, for example, an application onto at least a part of the surface of a plant or plant part. It is appreciated that calcium carbonate may be applied to exterior plants, e.g. plants on a field, as well as to interior plants, e.g. plants in a greenhouse.

"Pre-harvest" application means that the plant protection product is applied before the plant is harvested, i.e. during growth of the plant. The expression "during growth of the plant" refers to the time period after the plant emerges and before it is harvested, for example, after bud burst and before harvesting, or during or after fruiting and before harvesting, or, in case of grapes, after bunch closure and before harvesting.

The pest to be controlled by the inventive use of calcium carbonate can be, for example, an insect, a nematode, a parasite, a gastropod, or a pathogen such as a fungus, a virus, or a bacterium. According to one embodiment of the present invention, the pest is a pathogen and/or an insect.

Within the context of the present invention, the term "pathogen" designates a pathogen of a plant in general, i.e. an infectious organism capable of proliferation that causes a disease or an illness in a plant. Examples of plant pathogens are fungi, oomycetes, bacteria, viruses, viroids, virus-like organisms, phytoplasmas, or protozoa.

According to one embodiment of the present invention, use of calcium carbonate as plant protection product for topical, pre-harvest application is provided, wherein the plant protection product controls a pathogen proliferation.

According to one embodiment of the present invention, the pathogen is a fungus. Examples of a fungus that may be controlled by calcium carbonate are *Botrytis* such as *Botrytis cinerea, Botrytis paeoniae,* or *Botrytis tulipae, Erysiphe* such as *E. cichoracearum, E. cruciferarum, E. lycopersici, E. necator, E. pisi,* and *E. heraclei, Leveillula* such as *Leveillula taurica, Sphaerotheca* such as *Sphaerotheca fuliginea* or *Sphaerotheca macularis, Rasutoria* such as *Rasutoria abietis, Microsphaera* such as *Microsphaera penicillata* or *Microsphaera alphitoides, Podosphaera* such as *Podosphaera* spp. *Kunze, Peronospora* such as *Peronospora parasitica, Phytophthora* such as *Phytophthora infestans, Pseudoperonospora* such as *Pseudoperonospora cubensis, Sclerotinia* such as *Sclerotinia sclerotiorum,* or *Plasmopara* such as *Plasmopara viticola.* According to a preferred embodiment of the present invention, the pathogen is *Botrytis* and/or *Sclerotinia,* and more preferably *Botrytis cinerea.*

According to another embodiment of the present invention, use of calcium carbonate as plant protection product for topical, pre-harvest application is provided, wherein the plant protection product controls an insect. Examples of an insect that may be controlled by calcium carbonate are diptera-, lepidoptera-, coleopteran-, sternorrhyncha-, auchenorrhyncha-, thysanoptera-, heteroptera- and hymenoptera- species. According to a preferred embodiment the pest is a fly, and more preferably *Drosophila suzukii.*

According to one embodiment of the present invention, use of calcium carbonate as plant protection product for topical, pre-harvest application is provided, wherein the plant protection product controls a pathogen proliferation and an insect. Preferably the pathogen is a fungus, more preferably *Botrytis* and/or *Sclerotinia,* most preferably *Botrytis cinerea,* and the insect is *Drosophila suzukii.*

It will be appreciated that calcium carbonate can be used for any kind of plant as plant protection product in the meaning of the present invention. Plants that may especially benefit from the inventive use are, for example, agricultural and horticultural crops.

According to one embodiment, the plant protection product is for plants selected from the group consisting of rosaceae, theobroma cacao, grapes, stone fruits, pome fruits, berries, citrus fruits, legumes, solanaceae crops, brassicaceae crops, cucurbit crops, liliaceous crops, bananas, papayas, mangos, and passion fruits. According to a preferred embodiment the plant protection product is for plants selected from the group consisting of grapes, stone fruits, pome fruits, berries, citrus fruits, bananas, papayas, mangos, and passion fruits, and most preferably for grapes. The term "grapes" as used herein refers to any kind of grapevine, for example, *vitis vinifera, vitis labrusca, vitis riparia, vitis aestivalis, vitis rotundifolia, vitis rupestris, vitis coignetiae, vitis amurensis,* or *vitis* vulpine, and especially to cultivated grapes such as table grapes or wine grapes. However, the inventive use of calcium carbonate should not be limited to the above-mentioned plants.

The inventors of the present invention surprisingly found that calcium carbonate is useful for plant protection in that it can control a pest, and especially a fungus and/or an insect, during the growth of a plant, if it is applied topically onto a plant before harvesting. Compared to conventional plant protection products, calcium carbonate is nontoxic and degradable in the environment. Therefore, it can be applied in organic farming and during growth periods of a plant, in which the application of conventional synthetic pesticides is typically prohibited to avoid toxic residues in the later harvested plant products. It will be appreciated that the inventive effect of calcium carbonate relates to the employed calcium carbonate itself, but is not a result of any surface coatings or materials adsorbed to the surface of the calcium carbonate.

The inventors also found that calcium carbonate can be especially useful for controlling a pest, and in particular a pathogen such as a fungus, in plants, which have fruits that grow closely to each other, and may touch each other as the fruit growing proceeds. An example for such plants are grapes, which form fruit clusters during growth, wherein the grapes touch each other and voids are generated within the fruit cluster during further grow of the grapes. In said voids between the grapes, water can be built up, for example, from mist or rain and persist for a longer period of time, which may create an excellent microclimate for the growth of a pathogen such as a fungus, once the void is warmed-up by the sun.

Furthermore, it was found by the inventors that the use of calcium carbonate as plant protection product provides the possibility of controlling *Botrytis cinerea* and *Drosophila suzukii* in combination, which are serious threats to grapes and other fruits and often occur together, since, for example, the damage caused by *Drosophila suzukii* may increase the risk for a secondary *Botrytis cinerea* infection.

According to one embodiment of the present invention, calcium carbonate is used in form of a composition. Said composition may comprise further alkaline salts and/or earth alkaline salts, and preferably sodium carbonate, sodium bicarbonate, potassium carbonate, magnesium carbonate, calcium chloride, calcium sulphate, calcium nitrate, calcium oxide, calcium hydroxide, or mixtures thereof. Said composition may also comprise additives such as surfactants, wetters, humectants, stickers, spreaders, stabilizers, phosphate salts, or colourants.

In some embodiments, for example, when the control of multiple pests is desired, calcium carbonate can be used in combination with one or more natural or synthetic plant protection products or pesticides.

According to one embodiment, calcium carbonate is used in form of a composition further comprising an additional pesticide, preferably a fungicide and/or an insecticide. For example, the additional pesticide may be selected from the group consisting of fluopyram, fenhexamid, fenpyrazamin, pyrimethanil, cyprodonil, fludioxonil, bixafen, trifloxystrobin, azoxystrobin, kresoxin-methyl, pyraclostrobin, fluazinam, iprodion, vinclozolin, procymidone, cyproconazole, chlorothalonil, captan, folpet, prochloraz, difenoconazole, tebuconazole, prothioconazole, 3-difluoromethyl-1-methyl-1H-pyrazole-4-carboxylic acid(9-isopropyl-1,2,3,4-tetrahydro-1,4-methano-naphthalen-5-yl)-amide, azoxystrobin, difenoconazole, mefenoxam, imazalil, tebuconazole, paclobutrazole, and mixtures thereof. In addition or alternatively, the additional pesticide may be selected from a pesticide permitted in organic farming. Examples of pesticides permitted in organic farming are ammonium carbonate, aqueous potassium silicate, boric acid, copper sulphate, copper hydroxide, copper oxide, copper oxychloride, sulphur, lime sulphur, sucrose octanoate esters, ferric phosphate, hydrated lime, hydrogen peroxide, or mixtures thereof.

Calcium carbonate may not only control a pest during plant grow but also may control a pest after the plant was harvested. According to one embodiment use of calcium carbonate as plant protection product for topical, pre-harvest application is provided, wherein the plant protection product controls a pest during plant growth and plant storage.

According to an alternative embodiment use of calcium carbonate as plant protection product for topical application is provided, wherein the plant protection product controls a pest during plant growth and/or plant storage, and wherein the calcium carbonate is used in form of a solid and/or in form of an aqueous suspension having a solids content of at least 1 wt.-%, based on the total weight of the aqueous suspension. According to another alternative embodiment use of calcium carbonate as plant protection product for topical post-harvest application is provided, wherein the plant protection product controls a pest during plant storage, and wherein the calcium carbonate is used in form of a solid and/or in form of an aqueous suspension having a solids content of at least 1 wt.-%, based on the total weight of the aqueous suspension. It will be appreciated that the aforementioned details and embodiments provided with respect to the calcium carbonate, particle size, compositions, combinations, and the use of calcium carbonate, also apply to these alternative embodiments.

According to one embodiment, use of calcium carbonate as plant protection product for topical, pre-harvest application is provided, wherein the plant protection product controls a pest, preferably a fungus and/or insect, during plant grow, and wherein the calcium carbonate is natural ground calcium carbonate, is in form of particles having a weight median particle size $d_{50}$ from 0.1 to 200 µm, preferably from 1 to 50 µm, and is used in form of an aqueous suspension having a solids content from 1 to 85 wt.-%, based on the total weight of the aqueous suspension. According to a preferred embodiment, the pest is *Botrytis* and/or *Sclerotinia*, and/or the pest is *Drosophila suzukii*, and the plant is selected from the group consisting of grapes, stone fruits, pome fruits, berries, citrus fruits, bananas, papayas, mangos, and passion fruits, and most preferably the plant is selected from grapes.

Method of Protecting a Plant

According to a further aspect of the present invention, a method of protecting a plant by controlling a pest during plant growth is provided, wherein the method comprises the step of topically applying calcium carbonate onto at least a part of a plant before harvesting.

The calcium carbonate may be applied onto at least a part of a plant in liquid or solid form using conventional methods and equipment. Suitable application methods include dusting, sprinkling, seedling coating, foliar spraying, misting, or atomizing.

According to one embodiment, the calcium carbonate is in solid form and is applied to at least a part of a plant by dusting. According to another embodiment, the calcium carbonate is in form of an aqueous suspension and is applied to at least a part of a plant by spraying, preferably by a pressurized sprayer.

A skilled person will apply the calcium carbonate according to the need, in accordance with the type of plant and crop to be protected and in accordance with the pest to be controlled, while preparing efficient concentrations and employing suitable dilutions. Optimal use of the calcium carbonate may involve repeated application of calcium carbonate.

According to one embodiment of the present invention, the calcium carbonate is applied in an amount from 500 mg/m$^2$ to 50 g/m$^2$ of planted field area, preferably from 1 g/m$^2$ to 25 g/m$^2$ of planted field area, and more preferably from 8 g/m$^2$ to 16 g/m$^2$ of planted field area.

The calcium carbonate may be applied prophylactically to at least a part of a plant, or may be administered once a target pest has been identified in the particular plant to be protected. Calcium carbonate may be applied either earlier or later in the season, preferably just before the fruit starts to ripen.

According to one embodiment of the present invention, calcium carbonate is applied onto at least a part of a plant after bud burst and before harvesting, preferably during and/or after flowering and before harvesting, and more preferably before and/or during ripening and before harvesting. In case the plant to be protected is a grape, calcium carbonate may be preferably applied just before and/or during and/or after bunch closure and before harvesting.

The application of calcium carbonate can be made to either the whole plant canopy or just to the area in the canopy where the flowers and developing fruits are concentrated. According to one embodiment, the plant to be protected is a grape and the calcium carbonate is applied to the bunchline of the grape.

Calcium carbonate may be applied several times in order to increase efficiency. Reapplication of calcium carbonate may also be necessary after rain. According to one embodiment the calcium carbonate is applied at least one time, preferably at least two times, before harvesting.

According to one preferred embodiment, a method of protecting a plant by controlling a pest during plant growth is provided, wherein the plant is a grape and the method comprises the step of topically applying calcium carbonate onto at least a part of the plant just before and/or during bunch closure. According to another preferred embodiment, a method of protecting a plant by controlling a pest during plant growth is provided, wherein the plant is a grape and the method comprises the step of topically applying calcium carbonate onto at least a part of the plant just before and/or during bunch closure and during the colour change of the grapes. Preferably, the pest is a fungus and/or an insect, and more preferably the pest is *Botrytis* and/or *Sclerotinia* and/or the pest is *Drosophila suzukii*.

The bunch closure is a distinct point in time of a grapevine's growth phase, on which the berries have finished their growing and start to touch each other and the grape is closing. Applying the inventive plant protection product just before or during bunch closure can have the advantage that the interior of the grapes is still accessible, and thus, can also be treated by the plant protection product.

The colour change of the grapes indicating that the ripening starts, is a further distinct point in time of a grapevine's growth phase. This point in time is also called "véraison", which is a French term meaning "change of colour of the grape berries". Véraison represents the transition from berry growth to berry ripening, and many changes in berry development occur at véraison. For example, after véraison or colour chance of the grapes, the fruit acidity decreases and sugars are accumulated. As ripening continues, the fruit becomes attractive to animals due to changes in aroma from acidic to sweet with fruitiness.

The occurrence of these two specific events, i.e. bunch closure and colour change of the grapes, will depend on the plant variety and the location and are well known to the skilled person. A wine producer, for example, will readily recognize these points in time.

In addition, calcium carbonate may be applied immediately after harvest, for example, to further control the pest during storage of the plant or during wintering of the plant.

According to one embodiment the calcium carbonate is additionally applied after harvesting, preferably at least one time, more preferably at least two times.

According to one embodiment of the present invention, a method of protecting a plant by controlling a pest during plant growth and plant storage is provided, wherein the method comprises the step of topically applying calcium carbonate onto at least a part of a plant before harvesting, and optionally after harvesting. Alternatively, the calcium carbonate may be applied onto at least a part of a plant after harvesting. According to an alternative embodiment of the present invention, a method of protecting a plant by controlling a pest during plant storage is provided, wherein the method comprises the step of topically applying calcium carbonate onto at least a part of a plant after harvesting, wherein the calcium carbonate is in form of a solid and/or in form of an aqueous suspension having a solids content of at least 1 wt.-%, based on the total weight of the aqueous suspension. It will be appreciated that the afore-mentioned details and embodiments provided with respect to the calcium carbonate, particle size, compositions, combinations, the use of calcium carbonate, and the method of protecting a plant also apply to these alternative embodiments.

The foregoing explanations and embodiments also apply in case calcium carbonate is applied onto at least a part of a plant in form of a composition and/or in combination with an additional plant protection product. The scope and interest of the invention will be better understood based on the following examples which are intended to illustrate certain embodiments of the invention and are non-limitative.

EXPERIMENTS

1. Materials

In the following, materials implemented in the examples are described.

P1: Fluopyram (Moon Privilege, Bayer AG, Switzerland), suspension-concentrate, concentration: 500 g/l.

P2: Fenhexamid (Teldor WG 50, Bayer AG, Switzerland), water-dispersible granulate, concentration: 51%.

P3: Cyprodinil and Fludioxonil (Switch®, Syngenta, Switzerland), water-dispersible granulate, concentration: 37.5 wt.-% Cyprodinil and 25.0 wt.-% Fludioxonil.

P4: Fenpyrazamin (Prolectus®, Omya Agro AG, Switzerland), water-dispersible granulate, concentration 50%.

P5: Pyrimethanil (Scala®, BASF AG, Germany), suspension-concentrate, concentration: 400 g/l.

P6: Natural ground calcium carbonate ($d_{50}$=1.6 µm, $d_{98}$=6 µm), powder, commercially available from Omya AG.

P7: Pyrethrine (Parexan N, Omya Agro AG, Switzerland), emulsifiable concentrate, concentration: 5%.

P8: Spinosad (spinosyn A and spinosyn D) (Audienz, Omya Agro AG, Switzerland), suspension-concentrate, concentration: 480 g/l.

2. Experiments

Example 1

Field Trials on Grapes Regarding Efficiency Against *Botrytis cinerea*

Field trials in two different vineyards over two years including different wine grape varieties were conducted in the state Aargau, in Switzerland, which has an EPPO maritime climate zone.

Five different commercially available plant protection products (P1 to P5) and the inventive plant protection product calcium carbonate (P6) were tested regarding their efficiency to control the fungus *Botrytis cinerea* in the vineyard. The size of a single test plot within a vineyard was 2.5 m×5 m (12.5 m²).

In every field trial, any one of the products P1 to P6 was tested on three different plots. As indicated in Table 1 below, the products P1 to P6 were applied according to two different application schemes, designated application scheme A and application scheme B. Application scheme A refers to an application of the plant protection product at the point in time on which the berries of the grapes started to touch (bunch closure). Application scheme B refers to an application of the plant protection product at the point in time on which the berries changed colour and started to ripen (véraison). As explained in detail above, the occurrence of the bunch closure and the véraison will depend on the plant variety and the location and is well known to the skilled person. A wine producer, for example, will readily recognize these points.

As can be gathered from Table 1 below, the plant protection products were either applied only once, namely at the point in time on which the berries of the grapes started to touch (application scheme A), or twice (application scheme A and B), namely first at the point in time on which the berries of the grapes started to touch (bunch closure) and second at the point in time on which the berries changed colour and started to ripen (véraison).

The substances were applied to the vineyard plots with a motor backpack sprayer (nozzle type: Yamaho, nozzle size: C-35, operation pressure: 3 bar, Maruyama, Japan), at a dose of 1 200 l/ha (120 ml/m²). Only the lower part of the vine plants was treated, i.e. the region where the grapes are, which is the typical procedure for controlling *Botrytis*.

The treatments and the amount of the applied substances are summarized in Table 1 below.

TABLE 1

Treatments against *Botrytis cinerea* carried out during the field trials.

| Treatment number | Plant protection product | Application scheme | Amount |
|---|---|---|---|
| 1 | — | — | — |
| 2 | P4 | A | 1.2 g/ha (0.12 g/m²) |
| 3 | P1 | A | 0.5 l/ha (50 µl/m²) |
| 4 | P2 | A | 1.5 kg/ha (0.15 g/m²) |
| 5 | P3 | A | 1.2 kg/ha (0.12 g/m²) |
| 6 (inventive) | P6 | A | 180 kg/ha (18 g/m²) |
| 7 | P4 | A | 1.2 kg/ha (0.12 g/m²) |
|   | P5 | B | 3 l/ha (300 µl/m²) |
| 8 | P5 | A | 3 l/ha (300 µl/m²) |
|   | P4 | B | 1.2 kg/ha (0.12 g/m²) |
| 9 | P1 | A | 0.5 l/ha (50 µl/m²) |
|   | P2 | B | 1.5 kg/ha (0.15 g/m²) |
| 10 | P4 | A | 1.2 kg/ha (0.12 g/m²) |
|   | P3 | B | 1.2 kg/ha (0.12 g/m²) |
| 11 | P2 | A | 1.5 kg/ha (0.15 g/m²) |
|   | P5 | B | 3 l/ha (300 µl/m²) |
| 12 (inventive) | P6 | A | 180 kg/ha (18.0 g/m²) |
|   | P6 | B | 180 kg/ha (18.0 g/m²) |
| 13 (inventive) | P6 | A | 120 kg/ha (12.0 g/m²) |
|   | P6 | B | 120 kg/ha (12.0 g/m²) |

The efficiency of the different treatments against *Botrytis cinerea* was evaluated by estimating the percentage of attacked berries based on 20 grapes of each plot. Three untreated plots were used as baseline to determine the efficiency of the different treatments. The results of the treatments for every vineyard are shown below and are the mean values derived from 3 plots.

Field Trial I—Grape Varieties: Riesling x Sylvaner

The percentage of attacked berries was evaluated one and a half months after the berries changed colour and started to ripen.

TABLE 2

Results of field trial I.

| Treatment number | Average affected proportion of the grapes [%] | Efficiency of treatment [%] |
|---|---|---|
| 1 | 51.50 | 0 |
| 2 | 41.00 | 21 |
| 3 | 15.57 | 69 |
| 4 | 31.92 | 38 |
| 5 | 41.70 | 17 |
| 6 (inventive) | 34.78 | 30 |
| 7 | 30.12 | 41 |
| 8 | 34.67 | 31 |
| 9 | 11.13 | 77 |
| 10 | 18.67 | 63 |
| 11 | 18.35 | 64 |
| 12 (inventive) | 19.05 | 63 |
| 13 (inventive) | 18.45 | 63 |

The pressure of *Botrytis cinerea* in this field trial was very high. 52% of the surface of the grapes was destroyed by *Botrytis cinerea* in the untreated control plots (treatment 1). Even the best treatment (treatment 9, P1 and P2) only reached an efficacy of 77%. All treatments with calcium carbonate (P6, treatments 6, 12 and 13) showed a significant effect. Treatment 6 where P6 was applied once (180 kg/ha) reached an efficacy of 30%, while treatments 12 and 13 reached both an efficacy of 63%. The lower dose used in treatment 13 did not result in a lower efficacy compared to the higher dose of treatment 12.

Field Trial II—Grape Variety: Pinot Noir

The percentage of attacked berries was evaluated one and a half months after the berries changed colour and started to ripen.

TABLE 3

Results of field trial II.

| Treatment number | Average affected proportion of the grapes [%] | Efficiency of treatment [%] |
|---|---|---|
| 1 | 8.97 | 0 |
| 2 | 4.15 | 54 |
| 3 | 2.48 | 72 |
| 4 | 6.50 | 28 |
| 5 | 4.08 | 55 |
| 6 (inventive) | 3.73 | 58 |
| 7 | 2.73 | 70 |
| 8 | 4.15 | 54 |
| 9 | 2.32 | 74 |
| 10 | 2.38 | 73 |
| 11 | 3.30 | 63 |
| 12 (inventive) | 2.55 | 72 |
| 13 (inventive) | 2.45 | 73 |

In the untreated control plots an average of 9% of the berries were damaged by *Botrytis cinerea* (treatment 1). The treatment with the comparative products P1 and P2 (treatment 9) reached the highest efficacy (74%), followed by the treatment with the comparative products P4 and P3 (treatment 10, 73%).

All treatments with calcium carbonate (P6, treatments 6, 12 and 13) showed a significant effect, and treatments 12 and 13, wherein P6 was applied two times showed an efficiency of 73% and 72%, which is in a similar range as the best results observed for the comparative products. The lower dose used in treatment 13 did not result in a significantly lower efficacy compared to the higher dose of treatment 12.

Field Trial III—Grape Variety: Gewürztraminer

The percentage of attacked berries was evaluated two months after the berries changed colour and started to ripen.

TABLE 4

Results of field trial III.

| Treatment number | Average affected proportion of the grapes [%] | Efficiency of treatment [%] |
|---|---|---|
| 1 | 6.10 | 0 |
| 2 | 1.57 | 74 |
| 3 | 0.90 | 85 |
| 4 | 1.02 | 83 |
| 5 | 1.30 | 79 |
| 6 (inventive) | 2.32 | 62 |
| 7 | 1.17 | 81 |
| 8 | 1.07 | 82 |
| 9 | 0.65 | 89 |
| 10 | 0.22 | 96 |
| 11 | 0.82 | 86 |
| 12 (inventive) | 1.98 | 68 |
| 13 (inventive) | 1.03 | 83 |

In the untreated control plots an average of 6.1% of the berries were damaged by *Botrytis cinerea* (treatment 1). The treatment with the comparative products P4 and P3 (treatment 10) reached the highest efficacy (96%), followed by the treatment with the comparative products P1 and P2 (treatment 9, 89%), P2 and P5 (treatment 11, 86%), and P1 (treatment 3, 85%).

All treatments with calcium carbonate (P6, treatments 6, 12 and 13) showed a significant effect, and a good efficiency against *Botrytis cinerea*.

Field Trial IV—Grape Varieties: Riesling x Sylvaner

The percentage of attacked berries was evaluated one and a half months after the berries changed colour and started to ripen.

TABLE 5

Results of field trial IV.

| Treatment number | Average affected proportion of the grapes [%] | Efficiency of treatment [%] |
|---|---|---|
| 1 | 35.73 | 0 |
| 2 | 6.60 | 82 |
| 3 | 3.45 | 90 |
| 4 | 2.25 | 93 |
| 5 | 4.52 | 86 |
| 6 (inventive) | — | — |
| 7 | 5.17 | 85 |
| 8 | 2.43 | 94 |
| 9 | 0.88 | 97 |
| 10 | 4.75 | 85 |
| 11 | 2.78 | 92 |
| 12 (inventive) | 6.00 | 83 |
| 13 (inventive) | — | — |

Just before harvest, about 35.7% of the berries were affected by *Botrytis cinerea* in the untreated control plots (treatment 1). The treatment with the comparative products P1 and P2 (treatment 9) reached the highest efficacy (97%), followed by the treatment with the comparative products P5 first and P4 afterwards (treatment 8, 94%).

The treatment with the inventive product P6 applied two times showed a good efficacy of 83%, which was comparable to the comparative products.

Field Trial V—Grape Variety: Pinot Noir

The percentage of attacked berries was evaluated two months after the berries changed colour and started to ripen.

TABLE 6

Results of field trial V.

| Treatment number | Average affected proportion of the grapes [%] | Efficiency of treatment [%] |
|---|---|---|
| 1 | 2.45 | 0 |
| 2 | — | — |
| 3 | 0.08 | 97 |
| 4 | — | — |
| 5 | 0.82 | 67 |
| 6 (inventive) | — | — |
| 7 | — | — |
| 8 | — | — |
| 9 | 0.27 | 89 |
| 10 | 0.43 | 82 |
| 11 | 0.67 | 73 |
| 12 (inventive) | 0.10 | 96 |
| 13 (inventive) | 0.12 | 95 |

In the untreated control plots an average of 2.5% of the berries were damaged by *Botrytis cinerea* (treatment 1). The treatment with the comparative product P1 (treatment 3) reached the highest efficacy (97%), followed by the treatments with the inventive product P6 (treatments 12 and 13, 96% and 95%). The lower dose used in treatment 13 did not result in a significantly lower efficacy compared to the higher dose of treatment 12.

Summary of Field Trials I to V

As can be gathered from Table 7 below, calcium carbonate showed a very good efficacy in all field trials. In most cases, the treatment with twice 180 kg/ha (treatment 12) did not show a significantly higher efficacy than the treatment with twice 120 kg/ha (treatment 13). The efficacy of the treatment with only once 180 kg/ha was lower in all field trials but still showed good efficacy.

TABLE 7

Summary of results of field trials I to V.

| Field trial | I | II | III | IV | V |
|---|---|---|---|---|---|
| Efficacy of treatment 6 (inventive) | 30% | 58% | 62% | — | — |
| Efficacy of treatment 12 (inventive) | 63% | 72% | 68% | 83% | 96% |
| Efficacy of treatment 13 (inventive) | 63% | 73% | 83% | — | 95% |
| Efficacy of best comparative treatment (treatment number) | 77% (9) | 74% (9) | 96% (10) | 97% (9) | 97% (3) |

Example 2

Field Trials on Pinot Noir Grapes Regarding Efficiency Against *Drosophila suzukii*

Two field trials in two different vineyards of the red wine grape variety Pinot noir were conducted in the state Aargau, in Switzerland, which has an EPPO maritime climate zone.

Two different commercially available insecticides (P7 and P8) and the inventive plant protection product calcium carbonate (P6) were tested regarding their efficiency to control the insect *Drosophila suzukii* in the vineyard. Furthermore, the plant protection products P1 and P2, which are effective against *Botrytis cinerea* but should not have an effect against *Drosophila suzukii*, were tested as an additional control. The size of a single test plot within a vineyard was 2.5 m×5 m (12.5 m$^2$).

In every field trial, any one of the products P1, P2, and P6 to P8 was tested on three different plots. As indicated in Table 8 below, the products P1, P2, and P6 to P8 were applied either twice, namely first at the point in time on which the berries of the grapes started to touch (bunch closure) and second at the point in time on which the berries changed colour and started to ripen (véraison) (application scheme A and B), or once, namely one month before harvesting (application scheme C). As explained in detail above, the occurrence of the bunch closure and the véraison will depend on the plant variety and the location and is well known to the skilled person. A wine producer, for example, will readily recognize these points.

The substances were applied to the vineyard plots with a motor backpack sprayer (nozzle type: Yamaho, nozzle size: C-35, operation pressure: 3 bar, Maruyama, Japan), at a concentration of 1 200 l/ha (120 ml/m$^2$). Only the lower part of the vine plants was treated, i.e. the region where the grapes are.

The treatments and the amount of the applied substances are summarized in Table 8 below.

TABLE 8

Treatments against *Drosophila suzukii* carried out during the field trials of Example 2.

| Treatment number | Plant protection product | Application scheme | Amount |
|---|---|---|---|
| 14 | — | — | — |
| 15 | P1 | A | 0.5 l/ha (50 μl/m$^2$) |
|  | P2 | B | 1.5 kg/ha (0.15 g/m$^2$) |
| 16 (inventive) | P6 | A | 180 kg/ha (18.0 g/m$^2$) |
|  | P6 | B | 180 kg/ha (18.0 g/m$^2$) |
| 17 (inventive) | P6 | A | 120 kg/ha (12.0 g/m$^2$) |
|  | P6 | B | 120 kg/ha (12.0 g/m$^2$) |
| 18 | P7 | C | 1.2 l/ha (0.12 ml/m$^2$) |
| 19 | P8 | C | 0.18 l/ha (18 μl/m$^2$) |

Field Trial VI

In the field trial VI the efficiency of the different treatments against *Drosophila suzukii* was evaluated by counting the number of affected berries on 10 grapes of each plot after the time period indicated in Table 9, respectively, below. The treatment with P1 and P2 was used as baseline to determine the efficiency of the different treatments, because it presumably had no effect against *Drosophila suzukii*. The results of the treatments are shown below and are the mean values derived from 3 plots.

TABLE 9

Results of field trial VI.

| Treatment number | Average number of affected berries per grape after 2 months [%] | Efficiency of treatment after 2 months [%] |
|---|---|---|
| 15 | 4.03 | 0 |
| 16 (inventive) | 0.63 | 84 |
| 17 (inventive) | 1.13 | 72 |

In the plots treated with P1 and P2 an average of 4.03% affected berries were found per grape. Calcium carbonate showed a very good efficacy against *Drosophila suzukii* (treatments 16 and 17, 84% and 72%).

Field Trial VII

In the field trial VII the efficiency of the different treatments against *Drosophila suzukii* was evaluated by counting the number of larvae of *Drosophila suzukii* on 20 grapes of each plot after the time period indicated in Table 10, respectively, below. Tree untreated plots were used as baseline to determine the efficiency of the different treatments. The results of the treatments are shown below and are the mean values derived from 3 plots.

TABLE 10

Results of field trial VII.

| Treatment number | Affected grapes after 14 days [%] | Efficiency of treatment after 14 days [%] | Affected grapes after 21 days [%] | Efficiency of treatment after 21 days [%] |
|---|---|---|---|---|
| 14 | 36.33 | 0 | 26.33 | 0 |
| 17 (inventive) | 2.67 | 92 | 4.00 | 79 |
| 18 | 9.33 | 73 | 39.33 | −189 |
| 19 | 2.00 | 93 | 17.00 | −42 |

In the untreated control plots an average of 36 larvae of *Drosophila suzukii* were found on 20 grapes per plot after 14 days (treatment 14). After 14 days all treatments showed a significant effect, the comparative product P8 (treatment 19) reached the highest efficacy with 93%, followed by the inventive product P6 with 92% (treatment 17).

After 21 days calcium carbonate still showed a very good efficacy while the comparative products were not effective against *Drosophila suzukii* anymore. The lower number of larvae found on the control plot after 21 days may be due to the fact that some of the larvae already have already pupated and flew away.

The invention claimed is:

1. A method of protecting a plant by controlling a pest during plant growth, wherein the method comprises the step of topically applying calcium carbonate in a form of a powder and/or an aqueous suspension having a solids content from 1 to 85 wt.-%, based on the total weight of the aqueous suspension, onto at least a part of a plant before harvesting, wherein the pest is *Botrytis* and/or *Drosophila suzukii*, and wherein the plant is selected from the group consisting of rosaceae, theobroma cacao, a grape vine, a stone fruit plant, a pome fruit plant, a berry plant, a citrus fruit plant, a brassicaceae plant, a cucurbit plant, a liliaceous plant, a banana plant, a papaya plant, a mango plant, and a passion fruit plant.

2. The method of claim 1, wherein the pest is *Botrytis*.

3. The method of claim 1, wherein the pest is *Botrytis cinerea*.

4. The method of claim 1, wherein the pest is *Drosophila suzukii*.

5. The method of claim 1, wherein the calcium carbonate is a natural ground calcium carbonate, a precipitated calcium carbonate, a functionalized calcium carbonate, a calcium carbonate containing mineral, or any mixture thereof.

6. The method of claim 1, wherein the calcium carbonate is a natural ground calcium carbonate selected from the group consisting of marble, chalk, dolomite, limestone, and any mixture thereof.

7. The method of claim 1, wherein the calcium carbonate is limestone.

8. The method of claim 1, wherein the calcium carbonate is in a form of particles having a weight median particle size $d_{50}$ from 0.1 to 200 μm.

9. The method of claim 1, wherein the calcium carbonate is in a form of particles having a weight median particle size $d_{50}$ from 0.6 to 100 μm.

10. The method of claim 1, wherein the calcium carbonate is in a form of particles having a weight median particle size $d_{50}$ from 1 to 50 μm.

11. The method of claim 1, wherein the calcium carbonate is applied in a form of an aqueous suspension having a solids content from 5 to 50 wt.-%, based on the total weight of the aqueous suspension.

12. The method of claim 1, wherein the calcium carbonate is applied in a form of an aqueous suspension having a solids content from 10 to 25 wt.-%, based on the total weight of the aqueous suspension.

13. The method of claim 1, wherein the calcium carbonate is in a form of an aqueous suspension, and is applied onto at least a part of the plant by spraying.

14. The method of claim 1, wherein the calcium carbonate is in form of a powder and is applied onto at least a part of the plant by dusting.

15. The method of claim 1, wherein the calcium carbonate is applied in an amount from 500 mg/m$^2$ to 50 g/m$^2$ of planted field area.

16. The method of claim 1, wherein the calcium carbonate is applied in an amount from 1 g/m$^2$ to 25 g/m$^2$ of planted field area.

17. The method of claim 1, wherein the calcium carbonate is applied in an amount from 8 g/m$^2$ to 16 g/m$^2$ of planted field area.

18. The method of claim 1, wherein the calcium carbonate is applied as a composition comprising calcium carbonate and one or more of alkaline salts and/or earth alkaline salts.

19. The method of claim 1, wherein the calcium carbonate is applied as a composition comprising calcium carbonate and one or more of sodium carbonate, sodium bicarbonate, potassium carbonate, magnesium carbonate, calcium chloride, calcium sulphate, calcium nitrate, calcium oxide, and calcium hydroxide.

20. The method of claim 1, wherein the calcium carbonate is used in combination with an additional plant protection product.

21. The method of claim 1, wherein the calcium carbonate is used in combination with an additional plant protection product that controls a pest during plant growth and plant storage.

22. The method of claim 1, wherein the calcium carbonate is used in combination with a fungicide and/or an insecticide.

23. The method of claim 20, wherein the plant protection product is for one or more of grapes, stone fruits, pome fruits, berries, citrus fruits, bananas, papayas, mangos, and passion fruits.

24. The method of claim 20, wherein the plant protection product is for grapes.

25. The method of claim 1, wherein the calcium carbonate is applied at least one time, or at least two times, before harvesting.

26. The method of claim 1, wherein the calcium carbonate is additionally applied at least one time, or at least two times, after harvesting.

27. A method of protecting a plant by controlling a pest during plant growth, wherein the method comprises the step of topically applying calcium carbonate in a form of a powder and/or an aqueous suspension having a solids content from 1 to 85 wt.-%, based on the total weight of the aqueous suspension, onto at least a part of a plant before harvesting, wherein the pest is *Drosophila suzukii.*

28. A method of protecting a plant by controlling a pest during plant growth, wherein the method comprises the step of topically applying calcium carbonate in a form of a powder and/or an aqueous suspension having a solids content from 1 to 85 wt.-%, based on the total weight of the aqueous suspension, onto at least a part of a plant before harvesting, wherein the pest is *Botrytis* and/or *Drosophila suzukii.*, and wherein the plant is a grape vine.

* * * * *